United States Patent
Moreton et al.

(10) Patent No.: US 6,802,874 B2
(45) Date of Patent: *Oct. 12, 2004

(54) LINEAR COMPOUNDS CONTAINING PHENOL AND SALICYLIC ACID UNITS

(75) Inventors: David John Moreton, Derbyshire (GB); Rodney John McAtee, Derbyshire (GB)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/462,322

(22) Filed: Jun. 16, 2003

(65) Prior Publication Data

US 2004/0123514 A1 Jul. 1, 2004

Related U.S. Application Data

(63) Continuation of application No. 09/802,500, filed on Mar. 9, 2001, now Pat. No. 6,596,038.

(51) Int. Cl.[7] .................................................. C10L 1/18
(52) U.S. Cl. ........................... 44/389; 44/386; 44/403; 508/479; 508/510; 560/57; 560/70; 562/468; 562/476; 562/477
(58) Field of Search ........................ 44/389, 403, 386; 508/331, 479, 510; 560/57, 70, 71; 562/468, 476, 477

(56) References Cited

U.S. PATENT DOCUMENTS

| | | | |
|---|---|---|---|
| 2,197,834 A | 4/1940 | Reiff et al. ................... 87/9 |
| 2,202,877 A | 6/1940 | Stevens et al. ................. 44/9 |
| 2,361,338 A | 10/1944 | Walters ....................... 44/78 |
| 3,155,463 A | 11/1964 | Andress, Jr. et al. ........... 44/62 |
| 3,215,727 A | 11/1965 | Turk et al. ................. 260/473 |
| 3,490,882 A | 1/1970 | Dunworth et al. .............. 44/73 |
| 3,586,629 A | 6/1971 | Otto et al. ................. 252/42.7 |
| 4,098,708 A | 7/1978 | Stuebe ..................... 252/51.5 |
| 4,233,035 A | 11/1980 | Allen et al. ................... 44/73 |
| 4,259,464 A | 3/1981 | Buriks et al. ............... 525/480 |
| 4,612,254 A | 9/1986 | Ginter et al. ............... 428/531 |
| 4,617,336 A | 10/1986 | Pastor et al. ............... 524/291 |
| 4,915,857 A | 4/1990 | Emert et al. ............... 252/32.7 |
| 5,114,601 A | 5/1992 | Cook et al. |
| 5,118,875 A | 6/1992 | Martella et al. ............. 568/727 |
| 5,205,946 A | 4/1993 | Cook et al. |
| 5,562,742 A | 10/1996 | Kulp et al. .................... 44/367 |
| 5,616,816 A | 4/1997 | Burges et al. ............... 568/267 |
| 5,688,998 A | 11/1997 | Ichimura et al. ............. 562/466 |
| 6,083,288 A | 7/2000 | Wolf .......................... 44/342 |
| 6,174,844 B1 | 1/2001 | Moreton ..................... 508/585 |
| 6,200,936 B1 | 3/2001 | Moreton ...................... 44/389 |
| 6,270,537 B1 | 8/2001 | Taylor ........................ 44/385 |
| 6,310,011 B1 | 10/2001 | Karn et al. ................. 508/460 |
| 6,340,659 B1 | 1/2002 | Kocsis et al. ............... 508/518 |
| 6,596,038 B1 * | 7/2003 | Moreton et al. ............... 44/389 |

FOREIGN PATENT DOCUMENTS

| | | |
|---|---|---|
| EP | 0 450 874 A2 | 10/1991 |
| EP | 0 461 554 B1 | 1/1994 |
| EP | 0 593 301 A1 | 4/1994 |
| EP | 0 708 171 A2 | 4/1996 |
| EP | 0 779 355 A2 | 6/1997 |
| EP | 0 779 356 A2 | 6/1997 |
| EP | 0 786 661 A2 | 7/1997 |
| JP | 62100520 | 5/1987 |
| WO | 97/31698 | 9/1997 |
| WO | 99/25677 | 5/1999 |
| WO | 99/25792 | 5/1999 |
| WO | 99/25793 | 5/1999 |

OTHER PUBLICATIONS

International Preliminary Examination Report; Application No. PCT/US02/04102; dated Nov. 26, 2003.

Schneider et al.; "Synthese und Eigenschaften von Macrocyclen aus Resorcinen sowie von entsprechenden Derivaten und Wirt–Gast–Komplexen"; Chemische Berichte, vol. 127, No. 12, Dec. 1994, pp. 2455–2469, XP002092722.

International Search Report, Application No. PCT/US02/04102, dated Jul. 29, 2002.

* cited by examiner

Primary Examiner—Cephia D. Toomer
(74) Attorney, Agent, or Firm—Neil A. DuChez; Teresan W. Gilbert

(57) ABSTRACT

The invention disclosed herein relates to linear compounds in the form of oligomers or polymers containing unsubstituted or substituted phenol units and unsubstituted or substituted salicylic acid units. These compounds are useful as additives for lubricants and fuels. Metal salts of these compounds are useful as lubricant additives. A process for making these compounds is disclosed.

28 Claims, No Drawings

LINEAR COMPOUNDS CONTAINING PHENOL AND SALICYLIC ACID UNITS

This is a continuation of application Ser. No. 09/802,500, filed Mar. 9, 2001, now U.S. Pat. No. 6,596,038.

TECHNICAL FIELD

This invention relates to linear compounds in the form of oligomers or polymers containing unsubstituted or substituted phenol units and unsubstituted or substituted salicylic acid units. These compounds are useful as additives for lubricants and fuels. Metal salts of these compounds are useful as lubricant additives.

BACKGROUND OF THE INVENTION

In high speed aircraft, both civilian and military, the liquid fuel is combusted to produce power, but also is circulated in the aircraft as a heat exchange fluid to remove the excess heat generated at such speeds from other fluids such as lubricating oils used in the aircraft. The fuel is thus maintained for long periods at high temperatures. This results in discoloration and decomposition which produce soluble colored products and insoluble products such as gums, sediments and granular material. The insoluble products can form deposits that reduce the heat exchange capacity and can block filters potentially causing loss of power. Soluble colored by-products are unsightly and an indication of decomposition.

In some oil fired devices, such as boilers and slow heating cookers, e.g. the Aga type, kerosene fuel is passed down a narrow metal feed pipe to the combustion chamber where it is burnt. Parts of the pipe are sufficiently near the hot chamber for them to be heated to significant temperatures, resulting in the risk of thermal degradation of the fuel in the pipe, especially with slow feed rates and high residence times in the pipe. This degradation can form solid deposits which reduce the flow and ultimately stop it, causing the combustion to stop. To overcome this manufactures of such devices have for many years recommended to their users that at least once each six months such pipe parts are cleaned of solid deposits of coke or other materials.

The problem therefore is to provide enhanced thermal stability to these fuels. The present invention provides a solution to this problem. The addition of the inventive compounds to these fuels enhances the thermal stability of such fuels.

International publications WO 99/25677 and WO 99/25793 disclose calixarenes containing within the calixarene ring at least one salicylic acid. The use of these compounds as fuel additives and lubricant additives is disclosed. Metal salts of these compounds as well as the use of such metal salts as lubricant additives are disclosed. These references indicate that in order to provide the calixarene ring structure it is necessary to use a reaction mixture containing at least 50% by weight solvent, preferably at least 80% by weight solvent, more preferably at least 90% by weight solvent. The references indicate that at solvent concentrations well below 50% by weight linear molecules are formed.

SUMMARY OF THE INVENTION

This invention relates to a linear compound comprising m units of formula (I)

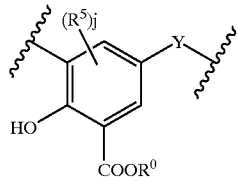

(I)

and n units of the formula (II)

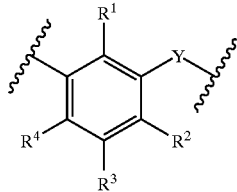

(II)

joined together, each end of the compound having a terminal group which is independently one of the following

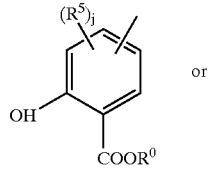

(III)

or

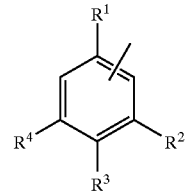

(IV)

wherein in formulae (I)–(IV), Y is a divalent bridging group which may be the same or different in each unit; $R^0$ is hydrogen or a hydrocarbyl group, $R^5$ is hydrogen or a hydrocarbyl, j is 1 or 2; $R^3$ is hydrogen, a hydrocarbyl or a hetero-substituted hydrocarbyl group; either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; m is at least 1; n is at least 2; the ratio of m to n ranges from about 0.1:1 to about 2:1, the total of m+n is at least 3; the linear compound containing at least one block unit containing at least two units corresponding to formula (II) attached to each other, the linear compound being formed in a reaction mixture optionally containing an organic solvent, the concentration of the organic solvent in the reaction mixture being up to about 48% by weight of the reaction mixture. The invention further provides for metal salts of the foregoing compounds. The linear compounds are useful as fuel and lubricant additives. The salts are useful as lubricant additives.

The inventive linear compounds, at least in one embodiment, are useful in the inventive lubricating oil compositions as surfactants and/or antioxidants. They are useful in the inventive fuel compositions, at least in one embodiment, as thermal stabilizers.

The metal salts of the inventive linear compounds are useful in the inventive lubricating oil compositions, at least in one embodiment, as detergents. The metal salts are also useful, at least in one embodiment, in reducing black paint in low- or medium-speed diesel engines.

DESCRIPTION OF THE PREFERRED EMBODIMENTS

The term "hydrocarbyl" denotes a group having a carbon atom directly attached to the remainder of the molecule and having a hydrocarbon or predominantly hydrocarbon character within the context of this invention. Such groups include the following:

(1) Purely hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc.

(2) Substituted hydrocarbon groups; that is, groups containing non-hydrocarbon substituents which do not alter the predominantly hydrocarbon character of the group. Those skilled in the art will be aware of suitable substituents. Examples include hydroxy, nitro, cyano, alkoxy, acyl, etc.

(3) Hetero groups; that is, groups which, while predominantly hydrocarbon in character, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

The terms "hydrocarbon" and "hydrocarbon-based" have the same meaning and can be used interchangeably with the term hydrocarbyl when referring to molecular groups having a carbon atom attached directly to the remainder of a molecule.

The term "lower" as used herein in conjunction with terms such as hydrocarbyl, alkyl, alkenyl, alkoxy, and the like, is intended to describe such groups which contain a total of up to 7 carbon atoms.

The term "oil-soluble" refers to a material that is soluble in mineral oil to the extent of at least about one gram per liter at 25° C.

The term "TBN" refers to total base number. This is the amount of acid (perchloric or hydrochloric) needed to neutralize all or part of a material's basicity, expressed as milligrams of KOH per gram of sample.

The Linear Compounds

The inventive linear compounds are in the form of linear oligomers or polymers. These compounds are comprised of units represented by formulae (I) and (II) connected to each other. At each end of the compound is a terminal group which is independently represented by the formulae (III) or (IV). The units represented by formulae (I) and (II) may be distributed in random or block patterns, with the proviso that at least one block of units consisting of two or more units represented by formula (II) must be present. For example, the linear compounds must include one or more block of units corresponding to -(II)(II)-, -(II)(II)(II)-, -(II)(II)(II)(II)-, etc. Examples of the inventive compounds include the following (III)-(II)-(II)-(II)-(I)-(II)-(III)
(III)-(II)-(I)-(I)-(II)-(II)-(II)-(IV)
(IV)-(I)-(I)-(II)-(II)-(II)-(I)-(IV)
(III)-(II)-(II)-(I)-(II)-(II)-(III)
(IV)-(I)-(II)-(II)-(II)-(II)-(II)-(IV)
(III)(II)(II)(II)(II)(II)(II)(I)(II)(II)(II)(IV)
(IV)((II))$_{10}$(I)((II))$_{5}$(I)(I)((II))$_{8}$(I)(IV)
(III)((I))$_{5}$(II)((I))$_{10}$(II)(II)(II)(IV)
(IV)((II))$_{20}$(I)((II))$_{10}$(I)(IV)
(IV)((II))$_{40}$(I)(I)(II)$_{5}$(IV)

The total number of units represented by formula (I) in the inventive linear compound is m, and the total number of units represented by formula (II) is n. m is at least 1. n is at least 2. The total of m+n is at least 3, and in one embodiment at least about 4, and in one embodiment at least about 5, and in one embodiment at least about 6, and in one embodiment at least about 7, and in one embodiment at least about 8. The total of m+n may range from 3 to about 50, and in one embodiment about 4 to about 50, and in one embodiment about 5 to about 50, and in one embodiment about 6 to about 50, and in one embodiment about 7 to about 50, and in one embodiment about 8 to about 50, and in one embodiment 3 to about 40, and in one embodiment 3 to about 30, and in one embodiment 3 to about 20. The ratio of m to n ranges from about 0.1:1 to about 2:1, and in one embodiment about 0.1:1 to about 1:1, and in one embodiment about 0.1:1 to about 0.5:1, and in one embodiment 0.1:1 to about 0.3:1, and in one embodiment about 0.14–0.15:1.

In formulae (I) and ((I), each Y may independently be represented by the formula $(CHR^6)_d$ in which $R^6$ is either hydrogen or hydrocarbyl and d is an integer which is at least 1. In one embodiment, $R^6$ contains 1 to about 6 carbon atoms, and in one embodiment 1 or 2 carbon atoms, and in one embodiment it is methyl. In one embodiment, d is from 1 to about 4. Y may optionally be sulphur rather than $(CHR^6)_d$ in up to 50% of the units, such that the amount of sulphur incorporated in the molecule is up to 50 mole %. In one embodiment, the amount of sulphur is between 8 and 20 mole %, and in one embodiment the compound is sulphur-free.

In formulae (I) and (III), $R^0$ is hydrogen or a hydrocarbyl (e.g., alkyl) group of 1 to about 6 carbon atoms, and in one embodiment 1 or 2 carbon atoms. $R^5$ is hydrogen or a hydrocarbyl group of 1 to about 100 carbon atoms, and in one embodiment 1 to about 60 carbon atoms, and in one embodiment 1 to about 30 carbon atoms, and in one embodiment 1 to about 18 carbon atoms, and in one embodiment 1 to about 12 carbon atoms, and in one embodiment 1 to about 6 carbon atoms.

In formulae (II) and (IV), $R^3$ is hydrogen or a hydrocarbyl of 1 to about 100 carbon atoms, and in one embodiment 1 to about 60 carbon atoms, and in one embodiment 1 to about 30 carbon atoms, and in one embodiment 1 to about 18 carbon atoms, and in one embodiment about 12 carbon atoms. $R^3$ may be dodecyl or derived from propylene tetramer. $R^3$ may be hetero-substituted. The hetero atoms or groups may be —O— or —NH—. In one embodiment, $R^3$ is an alkoxyalkyl group.

In formulae (II) and (IV), either $R^1$ is hydroxyl and $R^2$ and $R^4$ are independently either hydrogen, hydrocarbyl or hetero-substituted hydrocarbyl, or $R^2$ and $R^4$ are hydroxyl, and $R^1$ is either hydrogen, hydrocarbyl or hetero-substituted hydrocarbyl. The hydrocarbyl and hetero-substituted hydrocarbyl groups independently contain 1 to about 100 carbon atoms, and in one embodiment 1 to about 60 carbon atoms, and in one embodiment 1 to about 30 carbon atoms, and in one embodiment 1 to about 18 carbon atoms, and in one embodiment 1 to about 12 carbon atoms, and in one embodiment 1 to about 6 carbon atoms. The hetero substituants may be —O— or —NH—.

In one embodiment, Y is $CH_2$; $R^1$ is hydroxyl; $R^2$ and $R^4$ are hydrogen; $R^3$ is a hydrocarbyl group of about 6 to about 60 carbon atoms, and in one embodiment about 6 to about 30 carbon atoms, and in one embodiment about 6 to about 18 carbon atoms, and in one embodiment about 12 carbon atoms; $R^0$ is hydrogen; $R^5$ is hydrogen; j is 1; and m+n has a value of at least 5, and in one embodiment at least 6, and in one embodiment at least about 8; and m is 1 or 2, and in one embodiment m is 1.

In one embodiment, either or both of the terminal groups represented by the formulae (III) and (IV) has a —$CH_2OH$ group attached to the aromatic ring in an ortho position relative to the hydroxyl group.

The process for making the inventive linear compounds comprises reacting together optionally in an organic solvent, in the presence of a basic catalyst, compounds of the formulas (Ia) and (IIa)

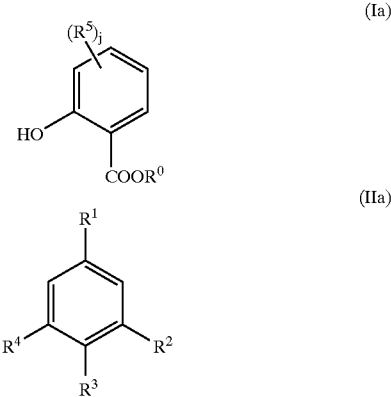

with an aldehyde of the formula O=$CHR^6$, and optionally sulphur; where $R^0$ to $R^6$ and j are as defined previously.

The formaldehyde may be paraformaldehyde, an aqueous solution of aldehyde (formalin), or a solution of an aldehyde in methanol.

The basic catalyst may be an alkali or alkaline earth metal hydroxide such as sodium hydroxide, potassium hydroxide, and the like; ammonia; or a hindered amine. The hindered amines that are useful include tetra alkyl ammonium hydroxides such as tetra methyl ammonium hydroxide, tetrabutyl ammonium hydroxide, and the like, as well as the trialkyl monoamines such as triethyl amine, and the like. The molar ratio of the basic catalyst to the number of moles of compound represented by formula (IIa) may range from about 0.005:1 to about 0.5:1, and in one embodiment about 0.02:1 to about 0.3:1, and in one embodiment about 0.02–0.04:1.

Alternatively, the basic catalyst may be a basic ion exchange resin such as the Amberlite resins provided by Rohn & Hass or the Dowex resins provided by Dow. These are macroreticular resins which are strongly basic in nature and have moderate porosities. Specific resins that may be used include Amberlite IRA 410 and Dowex 550OH. These resins may be used at a concentration of about 0.1 to about 30% by weight based on the overall weight of the reaction mixture, and in one embodiment about 0.1 to about 10% by weight.

A critical feature of this invention is the concentration of organic solvent (if used) in the reaction mixture which is up to about 48% by weight of the reaction mixture, and in one embodiment from about 5% to about 48% by weight, and in one embodiment about 15% to about 48% by weight, and in one embodiment about 30% to about 48% by weight of the reaction mixture. In one embodiment, the solvent comprises about 32% to about 46% by weight of the reaction mixture, and in one embodiment about 35% to about 45% by weight.

It is also critical that the compounds corresponding to formula (IIa) be permitted to oligomerize, at least partially, before adding the compounds corresponding to formula (Ia) to the reaction mixture. Thus, in conducting the inventive process, the compound corresponding to formula (IIa) is mixed with the solvent (if used) and reacted with the aldehyde in the presence of the basic catalyst prior to the addition of the compound corresponding to formula (Ia). As a result, the inventive linear compounds contain at least one block of two or more units corresponding to formula (II) linked to each other. For example, the inventive linear compounds may have one or more blocks of units corresponding to -(II)(II)-, -(II)(II)(II)-, -(II)(II)(II)(II)-, etc.

Metal Salts of the Linear Compounds

In one embodiment of the invention, low based, neutral or overbased salts of the inventive linear compounds are provided. The process for making the low-based or neutral salts comprises the steps of: (I) forming a mixture of components (A) and (C); and (II) adding a metal base (B) to the mixture of components (A) and (C), the addition of the metal base (B) to the mixture of (A) and (C) being in a single addition or in a plurality of additions, steps (I) and (II) being performed concurrently or sequentially.

Component (A) may be either (i) the inventive linear compound having at least one substituent hydroxyl group available for reaction with a metal base, or (ii) a low-based or neutral metal salt of the inventive linear compound having at least one substituent hydroxyl group available for reaction with the metal base.

Component (B) is a metal base. The metal moiety may be an alkali or alkaline earth metal, and in one embodiment an alkaline earth metal. The metal may be calcium, magnesium or barium, and in one embodiment it is calcium. The base moiety may be an oxide or a hydroxide. A calcium base may be added, for example, in the form of quick line (CaO) or in the form of slaked lime ($Ca(OH)_2$) or mixtures of the two in any proportion. Component (B) may be added in whole to the initial reactants or in part to the initial reactants and the remainder in one or more further additions at intermediate points during the reaction.

Component (C) is solvent comprising either component (C-1) or (C-2). Component (C-1) is either (i) a polyhydric alcohol having about 2 to about 4 carbon atoms, (ii) a di-($C_3$ or $C_4$) glycol, (iii) a tri-($C_2$–$C_4$) glycol or (iv) a mono- or poly-alkylene glycol alkyl ether of the formula:

$$R^1(OR^2)_fOR^3 \qquad (V)$$

wherein in the formula (V), $R^1$ is an alkyl group of 1 to about 6 carbon atoms, $R^2$ is an alkylene group of 1 to about 6 carbon atoms; $R^3$ is hydrogen or an alkyl group of 1 to about 8 carbon atoms, and f is an integer from 1 to about 6. Examples include the monomethyl or dimethyl ethers of ethylene glycol, diethylene glycol, triethylene glycol or tetraethylene glycol. A useful compound is methyl diglycol. Mixtures of glycol ethers and glycols may be used. The polyhydric alcohol may be either a dihydric alcohol, for example ethylene glycol or propylene glycol, or a trihydric alcohol, for example glycerol. The di- ($C_3$ or $C_4$) glycol may be dipropylene glycol, and the tri-($C_2$ to $C_4$) glycol may be triethylene glycol.

In one embodiment, component (C-1) further comprises: (a) a hydrocarbon solvent; or (b) either (i) water, (ii) a monohydric alcohol of 1 to about 20 carbon atoms, (iii) a ketone having up to 20 carbon atoms, (iv) a carboxylic ester having up to 10 carbon atoms, (v) an aliphatic, alicyclic or aromatic ether having up to 20 carbon atoms, or a mixture of two or more of (i) to (v). Examples include methanol, 2-ethyl hexanol, cyclohexanol, cyclohexanone, benzyl alcohol, ethyl acetate and acetophenone.

Component (C-2) is a monohydric alcohol of 1 to about 4 carbon atoms in combination with a hydrocarbon solvent.

The hydrocarbon solvent may be aliphatic or aromatic. Examples of suitable hydrocarbon solvents include toluene, xylene, naphtha and aliphatic paraffins, for example hexane, and cycloaliphatic paraffins.

In one embodiment, it is useful to incorporate an oil of lubbricating viscosity as a supplemental solvent. The oil may be an animal, vegetable or mineral oil. The oil may be a petroleum derived lubricating oil, such as a naphthenic base, paraffin base or mixed base oil. Solvent neutral oils may be used. The oil may be a synthetic oil. Suitable synthetic oils include synthetic ester oils, which oils include diesters such as di-octyl adipate, di-octyl sebacate and tri-decyladipate, or polymeric hydrocarbon oils, for example liquid polyisobutenes and poly-alpha olefins.

Useful solvents (C) include ethylene glycol, a mixture of ethylene glycol and 2-ethyl hexanol, and a mixture of methanol and toluene.

In one embodiment, the invention includes a process for the production of overbased metal salts of the inventive linear compounds which comprises the foregoing process for making a low based or neutral metal salt of the inventive linear compound but with the addition of the following step: (III) adding (D) carbon dioxide to the mixture of components (A), (B) and (C) subsequent to each addition of component (B). The carbon dioxide may be added in the form of a gas or a solid, preferably in the form of a gas. In gaseous form it may be blown through the reaction mixture.

The weight ratio of component (A) to component (C) may be from about 10 to about 65 parts by weight of (A) per 100 parts by weight of (C), and in one embodiment about 20 to about 60 parts by weight of (A) per 100 parts by weight of (C). The ratio of mole equivalents of component (B) to mole equivalents of component (A) may be from about 0.05 to about 20 mole equivalents of (B) per mole equivalent of (A), and in one embodiment about 0.08 to about 18 mole equivalents of (B) per mole equivalent of (A). The ratio of the number of moles of metal in component (B) to the number of moles of carbon dioxide in (D) may be from about 0.3 to about 1.6 moles of metal in (B) per mole of carbon dioxide in (D), and in one embodiment about 0.55 to about 1.3 moles of metal in (B) per mole of carbon dioxide in (D).

In one embodiment, the reaction mixture may include component (E). Component (E) is either (i) a carboxylic acid containing from about 6 to about 100 carbon atoms or an anhydride thereof, (ii) a di- or polycarboxylic acid containing from about 36 to about 100 carbon atoms or an anhydride thereof, (iii) a hydrocarbyl-substituted sulphonic acid or an anhydride thereof, (iv) a hydrocarbyl-substituted salicylic acid or an anhydride thereof, (v) a hydrocarbyl-substituted naphthenic acid or an anhydride thereof, (vi) a hydrocarbyl-substituted phenol or (vii) a mixture of any two of (i) to (vi). Component (E) may be added during step (I), (II) or (III), or prior to or subsequent to any of the foregoing steps. In one embodiment, component (E) is added during step (I). When component (E) is used, it may be used in an amount of up to about 40% by weight based on the combined weight of components (A), (B), (C), (D) and (E), and one embodiment from about 2 to about 38% by weight, and in one embodiment from about 12 to about 27% by weight.

Component (i) of component (E) may be an acid having the formula:

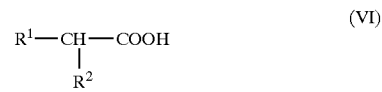

wherein in formula (VI), $R^1$ is an alkyl or alkenyl group of about 10 to about 24 carbon atoms, and $R^2$ is either hydrogen, an alkyl group of 1 to about 4 carbon atoms or a $-CH_2COOH$ group. $R^1$ may be an unbranched alkyl or alkenyl group. Examples of the saturated acids that may be used include capric, lauric, myristic, palmitic, stearic, isostearic, arachidic, behenic and lignoceric acids. Examples of the unsaturated acids that may be used include lauroleic, myristoleic, palmitoleic, oleic, gadoleic, erucic, ricinoleic, linoleic and linolenic acids. Mixtures of any of the foregoing acids may also be employed, for example, ripe top fatty acids. Suitable mixtures of acids are those commercial grades containing a range of acids, including both saturated and unsaturated acids. Such mixtures may be obtained synthetically or may be derived from natural products, for example, tall, cotton, ground nut, coconut, linseed, palm kernel, olive, palm, castor, soybean, sunflower, herring and sardine oils and tallow. In one embodiment, component (i) of component (E) is an acid anhydride, acid chloride or ester derivative of any of the foregoing acids.

Component (ii) of component (E) may be a polyisobutylene substituted succinic acid or a polyisobutylene substituted succinic anhydride. The molecular weight of such acid or anhydride may be in the range of about 300 to about 3000, and in one embodiment about 700 to about 1300.

As regards to components (iii), (iv), (v) and (vi) of component (E), the hydrocarbyl substituent may contain up to about 125 aliphatic carbon atoms, and in one embodiment about 6 to about 20 carbon atoms. Examples of suitable substituents include alkyl groups, for example hexyl, cyclohexyl, octyl, isoctyl, decyl, tridecyl, hexadecyl, eicosyl and tricosyl. Hydrocarbyl groups derived from the polymerization of both terminal and internal olefins, for example ethene, propene, 1-butene, isobutene, 1-hexene, 1-octene, 2-butene, 2-pentene, 3-pentene and 4-octene may be used. In one embodiment, the hydrocarbyl substituent is derived from polypropylene, poly-1-butene or polyisobutylene.

The reaction mixture may also include as component (F) a catalyst (or promoter) for the reaction. The catalyst may be an organic compound or an inorganic compound. The catalyst (F) is added during step (I), (II) or (III), or prior to or subsequent to any of the foregoing steps. In one embodiment, the catalyst (F) is added during step (I). When component (F) is used, the amount of component (F), added to the mixture of (A), (B), (C), (D) and optionally (E) ranges from about 0.1% to about 3% by weight based on the combined weight of the mixture, and in one embodiment about 2% by weight. Suitable organic compounds include (i) organic halides (e.g., chlorides, bromides, iodides) or (ii) organic alkanoates, which may be represented by the formula:

wherein in formula (VII), R is either an alkyl, aryl or alkaryl group which may have about 3 to about 20 carbon atoms, about 6 to about 20 carbon atoms, or about 7 to about 20 carbon atoms, respectively, or a halo-derivative thereof. X is either halogen, suitably chlorine, bromine or iodine, preferably chlorine, or the group OCOR$^1$ wherein R$^1$ is an alkyl group of 1 to about 4 carbon atoms. Alternatively, the organic halide may be an HX salt of an organic base, for example guanidine hydrochloride. An example of an organic halide represented by formula (VII) is octyl chloride. Mixtures of (i) and (ii) of component (F) may be employed. Suitable inorganic compound catalysts include inorganic halides, particularly inorganic chlorides, and inorganic alkanoates. Examples of suitable inorganic compound catalysts include calcium acetate, calcium chloride, ammonium chloride, ammonium acetate, aluminum chloride and zinc chloride. Provided that the catalyst is present during the carbonation step (i.e., step (III)), it may be added at any point in the process, though it is usually convenient to add the catalyst initially during step (I).

In order to produce an overbased salt from component (A)(i) or (A)(ii) it is necessary to react component (A) with components (B), (C) and (D), using the appropriate proportions of components (A) and (B) to achieve overbasing. Suitably component (B) may be added in one or more additions.

In order to produce a high TBN overbased metal salt of the inventive linear compound there may be employed an overbased metal salt of the inventive linear compound derived from one of the inventive linear compounds having a substituent group or groups available for reaction, and it is preferred to employ component (E), particularly either (E)(i) or (ii), and more particularly stearic acid, while at the same time adjusting the relative amounts of components (A) and (B) to a value sufficient to produce the desired high TBN metal salt.

The temperature at which the process is operated may be a temperature in the range from about 15 to about 200° C., and in one embodiment from about 50 to about 175° C. The selection of the optimum temperature within the aforesaid range is dependent in part on the nature of the solvent employed.

Generally, the process is operated in the presence of a lubricating oil. At the conclusion of the process it is preferred to recover the salt as a solution in lubricating oil by separating off volatile fractions, for example, by distillation at subatmospheric pressure. Finally, it is preferred to filter the solution. Alternatively, the solution may be centrifuged.

Salts produced by the above process may have TBNs of 100 mg KOH/g or below (i.e., low based or neutral metal salt of the inventive linear compounds). In one embodiment, the salts are overbased, in which case they generally have TBNs of at least about 200 mg KOH/g, and in one embodiment from about 200 to about 500 mg KOH/g, and in one embodiment from about 300 to about 500 mg KOH/g, and in one embodiment from about 350 to about 500 mg KOH/g, and in one embodiment from about 400 to about 500 mg KOH/g.

The salts may be supplied in the form of a concentrate. These concentrates are comprised of the foregoing salt and a substantially inert, normally liquid organic diluent such as mineral oil, synthetic oil (e.g., ester of dicarboxylic acid), naptha, alkylated (e.g., $C_{10}$–$C_{13}$ alkyl) benzene, toluene or xylene to form an additive concentrate. These concentrates usually contain from about 1% to about 99% by weight, and in one embodiment about 10% to about 90% by weight of the diluent.

Lubricating Oil Compositions

The inventive lubricating oil compositions are based on diverse oils of lubricating viscosity, including natural and synthetic lubricating oils and mixtures thereof. The lubricating oil compositions may be lubricating oils useful in industrial applications and in automotive engines, transmissions and axles. These lubricating oil compositions are effective in a variety of applications including crankcase lubricating oils for spark-ignited and compression-ignited internal combustion engines, including automobile and truck engines, two-cycle engines, aviation piston engines, marine and low-load diesel engines, and the like.

In one embodiment, the inventive lubricating oil composition is suitable for use in either low- or medium-speed engines, especially marine diesel engines. Typically such engines are 4-stroke trunk piston engines having an engine speed of 50–1,000 rpm, and in one embodiment 100–500 rpm, and a brake horse-power (BHP) per cylinder of 10–3,000, and in one embodiment 250–2,000. The engine can also be a 2-stroke cross-head engine having a speed of 40–1,000 rpm, and in one embodiment 100–500 rpm and a BHP per cylinder of 100–8,000.

The lubricating oil compositions employ an oil of lubricating viscosity which is generally present in a major amount (i.e. an amount greater than about 50% by weight). In one embodiment, the oil of lubricating viscosity is present in an amount greater than about 60% by weight, or greater than about 70% by weight, or greater than about 80% by weight.

In one embodiment, the oil of lubricating viscosity is selected to provide a lubricating composition having a kinematic viscosity of at least about 3.5, or at least about 4.0 cSt at 100° C. In one embodiment, the oil of lubricating viscosity is selected to provide a lubricating composition of at least an SAE gear oil viscosity number of about 60 or about 65. The lubricating composition may also have a so-called multigrade rating such as SAE 60W-80, 65W-80, 65W-90, 75W-80, 75W-90, 80W-90, 80W-140 or 85W-140. Multigrade lubricants may include a minor viscosity improving amount of a viscosity improver which is formulated with the oil of lubricating viscosity to provide the above lubricant grades. Useful viscosity improvers include polyolefins, such as polybutylene; rubbers, such as styrene-butadiene or styrene-isoprene; or polyacrylates, such as polymethacrylates. Useful viscosity improvers that are available commercially include Acryloid viscosity improvers available from Rohm & Haas; Shellvis rubbers available from Shell Chemical; and Lubrizol 3174 available from The Lubrizol Corporation.

In one embodiment, the oil of lubricating viscosity is selected to provide lubricating compositions with crankcase applications such as for gasoline and diesel engines. Typically, the lubricating compositions are selected to provide an SAE crankcase viscosity number of 10W, 20W or 30W grade lubricants. The lubricating compositions may also have a so-called multi-grade rating such as SAE 10W-30, 10W-40, 10W-50, etc. As described above, the multi-grade lubricants include a viscosity improver which is formulated with the oil of lubricating viscosity to provide the above lubricant grades.

The base oil for these lubricating oil compositions may be natural oils, synthetic oils, or a mixture thereof. The natural oils include animal oils and vegetable oils (e.g., castor oil, lard oil) as well as mineral lubricating oils such as liquid petroleum oils and solvent treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); poly(1-hexenes), poly-(1-octenes), poly(1-decenes), etc. and mixtures thereof; alkyl-benzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500–1000, diethyl ether of polypropylene glycol having a molecular weight of about 1000–1500, etc.) or mono- and polycarboxylic esters thereof, for example, the acetic acid esters, mixed $C_{3-8}$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butylphenyl) silicate, hexyl-(4-methyl-2-pentoxy) disiloxane, poly(methyl) siloxanes, poly-(methylphenyl) siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricants of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

The lubricating oil compositions of the present invention may have a TBN in the range from about 0.1 to about 100 mg KOH/g. When the composition is to be used in a 4-stroke trunk piston engine the TBN may be in the range from about 5 to about 70, and in one embodiment about 8 to about 50 mg KOH/g. When it is to be used in a 2-stroke cross-head engine and particularly for the crankcase, the TBN of the composition may be in the range from about 0.1 to about 15, and in one embodiment in the range from about 1 to about 10 mg KOH/g.

The inventive lubricating oil composition may be contaminated with a fuel oil which has a residual oil content. These fuel oils are suitable for use as diesel fuel oils. Fuel oils can in general be divided into two main categories, namely, distillates and heavy fuels. Distillates consist of one or more distilled fractions. Heavy fuels are fuels which comprise at least a proportion of a residual oil, that is an oil which remains after the distilled fractions have been removed from an unrefined oil. The composition of the residual oil will vary with the composition of the starting oil which is usually a crude oil and will also vary depending upon the distillation conditions. However, by its nature residual oil is of high molecular weight and high boiling point. Heavy fuels can also comprise, in addition to residual oil, distillates. However, heavy fuels generally comprise at least about 90% by weight, and in one embodiment at least about 95% by weight, and in one embodiment at least about 99% by weight residual oil. In one embodiment, the present invention relates to lubricating oil compositions that are contaminated with a heavy fuel. The amount of heavy fuel in the lubricating oil composition will vary. The lubricating oil composition may contain between about 0.1 to about 25% by weight, and in one embodiment about 0.1 to about 10% by weight, and in one embodiment about 0.3 to about 5% by weight, and in one embodiment, about 0.5 to about 3% by weight heavy fuel oil, which as defined above is a fuel oil which has a residual oil content. The use of these contaminated lubricating oil compositions in low- or medium-speed diesel engines such as 4-stroke piston engines and 2-stroke cross-head engines can lead to an engine cleanliness problem known as "black paint." By including the inventive linear compounds or metal salts thereof in these contaminated lubricating oil compositions the problem of black paint may be reduced or eliminated. Overbased metal salts of these compounds also function as high TBN detergents, thereby providing two functions in one product.

The lubricating oil compositions of the invention may contain at least 0.01% by weight of the inventive linear compound or metal salt thereof, and in one embodiment at least about 0.05% by weight, and in one embodiment at least about 0.1% by weight, and in one embodiment about 0.01 to about 10% by weight, and in one embodiment about 0.01 to about 7% by weight, and in one embodiment from about 0.01 to about 5% by weight, and in one embodiment about 0.05 to about 4% by weight, and in one embodiment about 0.1 to about 3% by weight.

In addition to the lubricating oil and the inventive linear compound or metal salt thereof, the inventive lubricating oil compositions may contain other additives known in the art. These include dispersants. Although any type of dispersant may be employed in the composition, a suitable dispersant is one derived from a hydrocarbyl-substituted succinic acid or anhydride by reaction with an amine, i.e. a hydrocarbyl-substituted succinimide such as a polyisobutylene substituted succinimide. These succinimides are well known in the art. Succinimide production is described in, for example, the following U.S. Pat. Nos. 2,992,708; 3,018,291; 3,024,237; 3,100,673; 3,219,666; 3,172,892; 3,272,746; 4,234,435; 4,904,410; and 6,165,235. Succinimide dispersants which are mono- or bis-succinimides may be employed.

The amount of dispersant used in the lubricating oil composition of the present invention may be in the range from about 0.01 to about 10% by weight, and in one embodiment from about 0.1 to about 5% by weight based on the weight of the lubricating oil composition.

In addition to the foregoing, the inventive lubricating oil composition may contain one or more additives conventionally employed lubricating oil compositions. Examples of such additives include additional detergents, foam inhibitors, extreme pressure/antiwear agents, rust inhibitors, antioxidents, and the like. The additional detergents that can be employed include hydrocarbyl-substituted alkaline earth metal phenates, salicylates, naphthenates, sulphonates or carboxylates, which may be neutral or overbased materials. The concentration of each of these when used may range from about 0.001% to about 20% by weight.

The lubricating oil composition of the invention may be prepared by diluting a concentrate comprising a solution of the inventive linear compound or metal salt thereof and optionally other useful additives such as those referred to hereinbefore in a suitable diluent with the base oil. As the diluent there may be employed any solvent for the product which is compatible both with the base oil and the inventive linear compound or salt thereof. The diluent may be a substantially inert, normally liquid organic diluent such as mineral oil, synthetic oil (e.g., ester of dicarboxylic acid), naptha, alkylated (e.g. $C_{10}$–$C_{13}$ alkyl) benzene, toluene or xylene. These concentrates usually contain from about 1% to about 99% by weight, and in one embodiment about 10% to about 90% by weight of the diluent.

In one embodiment, the inventive lubricating oil compositions contain a detergency improving amount of the inventive linear compound or metal salt thereof. In one embodiment, the inventive lubricating oil composition contains about 0.01 to about 10% by weight of the inventive linear compound or metal salt thereof based on the weight of the lubricating oil composition, and in one embodiment about 0.01 to about 5% by weight, and in one embodiment about 0.01 to about 2.5% by weight based on the weight of the lubricating oil composition.

As indicated above, the inventive linear compounds or metal salts thereof may be used for reducing black paint in low- or medium-speed diesel engines. The lubricating compositions used for these applications may comprise up to about 5% by weight, and in one embodiment from about 0.1% to about 3% by weight of a hydrocarbyl-substituted succinimide dispersant; from about 0.05 to about 5% by weight, and in one embodiment from about 0.1% to about 3% of a inventive linear compound or metal salt thereof; and a low-or medium-speed diesel engine lubricating oil.

Fuel Compositions

The fuel compositions of the present invention contain a major proportion of a normally liquid fuel, usually a hydrocarbonaceous petroleum distillate fuel such as motor gasoline as defined by ASTM Specification D439 or diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether.

Generally, the fuel compositions contain an amount of the linear compounds of this invention sufficient to provide the fuel with enhanced thermal stability properties; usually this amount is about 1 to about 1000 parts by weight of the inventive linear compound per million parts of fuel. In one embodiment, the concentration is from about 5 to about 1000 ppm, and in one embodiment about 5 to about 500 ppm, and in one embodiment about 5 to about 200 ppm, and in one embodiment about 10 to about 100 ppm.

The fuel composition may contain, in addition to the inventive linear compounds, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-di-tertiary-butyl-4-methylphenol, rust inhibitors such as alkylated succinic acids and anhydrides, bacteriostatic agents, gum inhibitors, metal deactivators, demulsifiers, upper cylinder lubricants and anti-icing agents. These additives may also include other ashless dispersants or detergents such as hydrocarbyl-succinimides, hydrocarbyl-amines, borated compounds, polether amines, and the like.

In one embodiment, the fuel is a jet fuel. The main component of jet fuel is usually a middle boiling distillate having a boiling point in the range about 150° C. to about 250° C. at atmospheric pressure. The fuel is typically kerosene which may be mixed with gasoline and optionally a light petroleum distillate. The jet fuel may comprise a mixture of gasoline and light petroleum distillate, e.g. in weight amounts of about 20–80:80–20, and in one embodiment about 50–75:50–25 which weight amounts may also be used for mixtures of gasoline and kerosene. The jet fuels for military use may be designated JP4 to JP8, e.g. JP4 as 65% gasoline/35% light petroleum distillate (according to US Mil. Spec. (MIL 5624G)), JP5, similar to JP4 but of higher flash point, JP7, a high flash point special kerosene for advanced supersonic aircraft and JP8, a kerosene similar to Jet AI (according to MIL 83133C). Jet fuel for civilian use may be a kerosene type fuel and designated Jet A or Jet A1. The jet fuel may have a boiling point of about 66–343° C., and in one embodiment about 66–316° C. (150–650° F., e.g. 150–600° F.), initial boiling point of about 149–221° C., e.g. 204° C. (300–430° F., e.g. 400° F.), a 50% boiling point of about 221–316° C. (430–600° F.) and a 90% boiling point of about 260–343° C. (500–650° F.) and API Gravity of 30–40. Jet fuel for turbojet use may boil at about 93–260° C. (200–500° F.) (ASTM D1655-59T). Further details on aviation fuels may be obtained from "Handbook of Aviation fuel Properties," Coordinating Research Council, Inc., CRC Report No. 530 (Society of Automotive Engineers Inc., Warrendale, Pa., USA, 1983) and on US military fuels, from "Military Specification for Aviation Turbine Fuels," MIL-T-5624P.

The jet fuel may be straight run kerosene optionally with added gasoline. The fuel may be purified to reduce its content of components contributing to or encouraging formation of colored products and/or precipitates. Among such components are aromatics, olefins and mercaptans. Thus the fuels may be purified to reduce their mercaptan content, e.g. Merox fuels and copper sweetened fuels, or to reduce their sulphur content, e.g. hydrofined fuels or Merifined fuels. Merox fuels are made by oxidation of the mercaptans and have a low mercaptan S content (e.g. less than 0.005% by weight S) such as about 0.0001–0.005% by weight but a higher disulphide S content (e.g. at most about 0.4%, or at most about 0.3% wt S such as about 0.05–0.25, e.g. 0.1–2%); their aromatic (e.g. phenolics) and olefins content are hardly changed. Hydrofined jet fuels are fuels in which the original fuel has been hydrogenated to remove at least some sulphur compound, e.g. thiols, and under severe conditions to saturate the aromatics and olefins; hydrofined jet fuels have very low sulphur contents (e.g. less than 0.01% S by weight). Merifined fuels are fuels that have been extracted with an organic extractant to reduce or remove their contents of sulphur compounds and/or phenols. The jet fuel may also contain metals, either following contact with metal pipes or carried over from the crude oil; examples of such metals are copper, nickel, iron and chromium usually in amounts of less than about one part per million (ppm), e.g. each in about 10–150 parts per billion (ppb) amounts. Merox and hydrofined fuels may be used in JP 4-8 jet fuels.

In one embodiment, the fuel is a fuel for combustion, especially for non motive purposes, e.g. power generation, steam generation and heating, especially for use in building and for cooking. The fuel is suitable for devices such as boilers and slow cookers in which there is localized preheating of the fuel before it is combusted. Such fuels are known as burning kerosene and may have the same physical properties as the kerosene based jet fuels described above, e.g. straight run kerosene, or kerosene modified to reduce its content of at least one of aromatics, olefins and sulphur compounds. The fuel may also contain metals as described above.

EXAMPLE 1

The following ingredients are used: 329 g dodecylphenol (1.256 moles, 1 equivalent); 24.1 g salicylic acid (0.175 mole, 0.14 equivalent); 116.2 g of 44% by weight formaldehyde in water (formalin) (1.70 moles, 1.356 equivalent); 4.84 g of a 50% by weight solution of potassium hydroxide in water (0.043 mole, 0.034 equivalent); and 380 g kerosene (solvent).

A reaction apparatus is set up using a one liter flange flask, a flange lid and clip, overhead stirrer with paddle and polytetrafluoroethylene stirrer gland, Dean & Stark trap and double surface condenser. The reactor contents are heated by an electric mantle/thermocouple/Eurotherm temperature controller system. The glassware from just above the mantle to just below the condenser is lagged with glass wool.

The one liter flask is charged with the dodecylphenol and kerosene and heated to 30° C. The potassium hydroxide solution is then added via a pressure equalizing dropping funnel. The solution becomes dark red brown in color. The reaction mixture is heated to 60° C., and the formalin is added over 30 minutes via a pressure equalizing dropping funnel. The reaction mixture is maintained at 60–65° C. until the concentration of free formaldehyde is less than 1.5% by weight (measured by titration). The salicylic acid is added and the reaction mixture is heated to 142° C. The water of reaction is drained off via the Dean & Stark trap. After 2.25 hours, 63 mls of water are collected. The reaction mixture is then maintained at 142° C. for 2.5 hours and 24 mls of additional water are collected. The reactor contents are cooled and poured into a container. The product is clear and golden. The yield is 703 g of product. The potassium content is 0.188% by weight. The product has a TBN of 2.9 mg KOH/g. NMR and dialysis indicates that the product consists of a mixture of linear compounds containing units derived from both dodecyl phenol and salicylic acid.

EXAMPLE 2

The following ingredients are used: 262.0 g dodecylphenol (1.00 mole, 1.00 equivalent); 19.32 g salicylic acid (0.140 moles, 0.140 equivalent); 110.0 g of 37% by weight solution of formaldehyde in water (formalin) (1.357 moles, 1.357 equivalent); 172 g of a 1M solution of tetrabutylammonium hydroxide in methanol (0.207 moles, 0.207 equivalent); and 339 g kerosene (solvent).

The apparatus used in Example 1 is used. The one liter flask is charged with all the ingredients apart from the tetrabutylammonium hydroxide solution, formalin and salicylic acid. The mixture is heated to 30° C. The tetrabutylammonium hydroxide solution is added via a pressure equalizing dropping funnel. The resulting solution has a clear yellow orange color. The reaction mixture is heated to 65° C. The formalin is added over a period of 35 minutes via a pressure equalizing dropping funnel. The color of the solution turns to a flesh color. The reaction mixture is held for 90 minutes at 65° C. The salicylic acid is added manually via a powder funnel. The reaction mixture is heated to 140° C. The methanol, water from the formalin solution and water of reaction are drained off via the Dean & Stark trap. After 1 hour and 50 minutes, 225 mls of water are collected. The reaction mixture is then held at 140° C. for 2.5 hours and additional 7 mls water are collected. The reactor contents are cooled and poured into a container. The product is dark brown. The yield of product is 684 g. The nitrogen content of the product is 0.206% by weight. The TBN of the product is 16.8 mg KOH/g. GPC and Mass spec. indicate that the product consists of a mixture linear compounds containing units derived from both dodecyl phenol and salicylic acid.

EXAMPLE 3

The products of Examples 1 and 2 are added to a jet fuel formulation at a concentration of 25 ppm active ingredients (i.e., organic solvent added but not included in calculation of 25 ppm) along with the following ingredients:

| | |
|---|---|
| Butylated hydroxy toluene | 25 ppm |
| N,N-bis salicylidene-1,2-diaminopropane | 2 ppm |
| Kerosene (solvent) | 75 ppm |
| Solvesso 150 (aromatic solvent supplied by Exxon) | 1.5 ppm |

A "control" or baseline formulation is also prepared wherein the jet fuel formulation is formulated without the inventive linear compound being present. Each jet fuel formulation is tested for thermal stability using a heated liquid process simulator. This test measures the differential pressure across a 17-micron filter at 335° C. fluid outlet temperature for five hours, followed by determination of total deposits on a heated stainless steel tube. The results are as follows:

| Product | Pressure (mmHg) | Time (minutes) | Deposits ($\mu g/cm^2$) |
|---|---|---|---|
| Control | 300 | 125 | 190 |
| Example 1 | 2.1 | 300 | 12 |
| Example 2 | 2.7 | 300 | 19 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for making a linear compound comprising:
reacting together, in an organic solvent, and in the presence of a basic catalyst, compounds of the formulas (Ia) and (IIa)

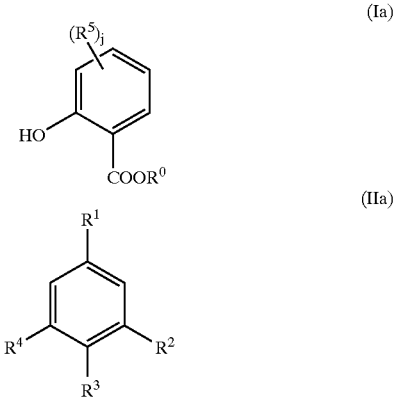

with an aldehyde represented by the formula O=CHR$^6$, and optionally sulphur; wherein R$^0$ is hydrogen or a hydrocarbyl group; R$^5$ is hydrogen or a hydrocarbyl group; j is 1 or 2; R$^3$ is hydrogen, a hydrocarbyl or a hetero-substituted hydrocarbyl group; either R$^1$ is hydroxyl and R$^2$ and R$^4$ are independently either hydrogen, hydrocarbyl or hetero-substituted hydrocarbyl or R$^2$ and R$^4$ are hydroxyl and R$^1$ is either hydrogen, hydrocarbyl or hetero-substituted hydrocarbyl; R$^6$ is hydrogen or a hydrocarbyl group; the process including an oligomerization step wherein the compound corresponding to formula (IIa) is permitted to react prior to the addition of the compound corresponding to formula (Ia); the organic solvent comprising up to about 48% by weight of the reaction mixture; the number of molar units of the compound represented by formula (Ia) being m, the number of molar units of the compound represented by formula (IIa) being n, wherein m is at least 1; n is at least 2; the ratio of m to n ranging from 0.1:1 to 2:1.

2. The process of claim 1 wherein the basic catalyst is alkali or alkaline earth metal hydroxide, ammonia, a hindered amine or a basic ion exchange resin.

3. The process of claim 1 wherein the basic catalyst is potassium hydroxide.

4. The process of claim 1 wherein the basic catalyst is ammonia or a hindered amine.

5. The process of claim 1 wherein R$^1$ is hydroxyl; R$^2$ and R$^4$ are independently either hydrogen, hydrocarbyl or hetero-substituted hydrocarbyl; R$^3$ is either hydrocarbyl or hetero-substituted hydrocarbyl; and R$^0$ and R$^5$ are hydrogen.

6. The process of claim 1 wherein m+n is 5 to 50.

7. The process of claim 1 wherein R$^3$ is dodecyl or octadecyl.

8. The process of claim 1 wherein: R$^0$ is hydrogen; R$^1$ is hydroxyl; R$^2$ and R$^4$ are hydrogen; R$^3$ is dodecyl; R$^5$ and R$^6$ are hydrogen, and j is 1.

9. A metal salt of the compound made by the process of claim 1 wherein the metal moiety of the metal salt is either an alkali or an alkaline earth metal.

10. A composition comprising a metal salt of the compound made by the process of claim 1 wherein the TBN for the composition is from 200 to 500 mg KOH/g.

11. A concentrate comprising the compound made by the process of claim 1 or a metal salt of said compound and an organic diluent, the concentration of the organic diluent ranging from 1 to 99% by weight.

12. A lubricating oil composition, comprising a minor amount of the compound made by the process of claim 1 or a metal salt of said compound, and a major amount of a lubricating oil.

13. The lubricating oil composition of claim 12 wherein the lubricating oil composition further comprises a contaminate amount of fuel oil having a residual oil content.

14. A fuel composition comprising a major amount of a normally liquid fuel and a minor amount of the compound made by the process of claim 1.

15. The fuel composition of claim 13 wherein the normally liquid fuel is jet fuel.

16. A process for making a metal salt, comprising the following steps:
(I) forming a mixture of components (A) and (C);
component (A) being the compound made by the process of claim 1;
component (C) being a solvent comprising either component (C-1) or (C-2);
component (C-1) being either (i) a polyhydric alcohol having 2 to 4 carbon atoms; (ii) a di-(C$_3$ or C$_4$) glycol, (iii) a tri-(C$_2$–C$_4$) glycol or (iv) a mono- or poly-alkylene glycol alkyl ether of the formula:

wherein the formula (V), R$^1$ is an alkyl group of 1 to 6 carbon atoms, R$^2$ is an alkylene group of 1 to 6 carbon atoms, R$^3$ is hydrogen or an alkyl group of 1 to 8 carbon atoms, and f is an integer from 1 to 6;
component (C-2) being a monohydric alcohol of 1 to 4 carbon atoms in combination with a hydrocarbon solvent; and
(II) adding a metal base (B) to the mixture of components (A) and (C), the addition of the metal base (B) to the mixture of (A) and (C) being in a single addition or in a plurality of additions, steps (I) and (II) being performed concurrently or sequentially.

17. The process of claim 16 with the additional step of:
(III) adding (D) carbon dioxide to the mixture of components (A), (B) and (C) subsequent to each addition of component (B).

18. The process of claim 16 wherein component (C-1) further comprises: (a) a hydrocarbon solvent; or (b) either (i) water, (ii) a monohydric alcohol of 1 to 20 carbon atoms, (iii) a ketone having up to 20 carbon atoms, (iv) a carboxylic ester having up to 10 carbon atoms, or (v) an aliphatic, alicyclic or aromatic ether having up to 20 carbon atoms, or mixture of two or more of (i) to (v).

19. The process of claim 17 wherein during step (I), (II) or (III), or prior to or subsequent to step (I), (II) or (III) the reaction mixture further comprises component (E); component (E) being either: a carboxylic acid or anhydride thereof containing 6 to 100 carbon atoms; (ii) a di- or polycarboxylic acid or anhydride thereof containing from 36 to 100 carbon atoms; (iii) a hydrocarbyl-substituted sulphonic acid or anhydride thereof; (iv) a hydrocarbyl-substituted salicylic acid or anhydride thereof; (v) a hydrocarbyl-substituted naphthenic acid or anhydride thereof; (vi) a hydrocarbyl-substituted phenol; or (vii) a mixture of two or more of (i) to (vi).

20. The process of claim 16 wherein said process is conducted at a temperature in the range of 15° C. to 200° C.

21. The process of claim 16 wherein the weight ratio of (A) to (C) ranges from 10 to 65 parts of (A) per 100 parts of (C).

22. The process of claim 16 wherein the mole equivalent ratio of component (B) to component (A) is from 0.05 to 20 mole equivalents of (B) per mole equivalent of (A).

23. The process of claim 17 wherein the ratio of the number of moles of metal in (B) to the number of moles of carbon dioxide in (D) is from 0.3 to 1.6 moles of metal in (B) per mole of carbon dioxide in (D).

24. The process of claim 19 wherein the amount of component (E) is up to 40% by weight based on the combined weight of components (A), (B), (C), (D) and (E).

25. The process of claim 1 wherein the organic solvent comprises from about 5% to about 48% by weight of the reaction mixture.

26. The process of claim 1 wherein the organic solvent comprises from about 15% to about 48% by weight of the reaction mixture.

27. The process of claim 1 wherein the organic solvent comprises from about 30% to about 48% by weight of the reaction mixture.

28. The process of claim 1 wherein the organic solvent comprises from about 35% to about 45% by weight of the reaction mixture.

* * * * *